(12) United States Patent
Nayak

(10) Patent No.: US 10,294,019 B2
(45) Date of Patent: May 21, 2019

(54) SYSTEM FOR PREPARING MEDICINAL BEVERAGES USING CARTRIDGE-TYPE BEVERAGE BREWERS

(71) Applicant: Vin Nayak, Morganville, NJ (US)

(72) Inventor: Vin Nayak, Morganville, NJ (US)

(73) Assignee: Raritan Pharmaceuticals Inc., East Brunswick, NJ (US)

( * ) Notice: Subject to any disclaimer, the term of this patent is extended or adjusted under 35 U.S.C. 154(b) by 336 days.

(21) Appl. No.: 15/238,802

(22) Filed: Aug. 17, 2016

(65) Prior Publication Data

US 2018/0050860 A1  Feb. 22, 2018

(51) Int. Cl.

| B65D 85/80 | (2006.01) |
|---|---|
| A61K 31/07 | (2006.01) |
| A47J 31/40 | (2006.01) |
| B65D 85/804 | (2006.01) |
| A61K 31/167 | (2006.01) |
| A61K 31/192 | (2006.01) |
| A61K 31/138 | (2006.01) |
| A61K 31/4748 | (2006.01) |
| A61K 31/137 | (2006.01) |
| A61K 31/4402 | (2006.01) |
| A61K 31/085 | (2006.01) |
| A61K 31/4045 | (2006.01) |
| A61K 31/704 | (2006.01) |
| A61K 31/225 | (2006.01) |
| A61K 31/702 | (2006.01) |
| A61K 31/522 | (2006.01) |
| A61K 31/593 | (2006.01) |
| A61K 31/355 | (2006.01) |
| A61K 31/202 | (2006.01) |
| A61K 31/385 | (2006.01) |
| A61K 31/714 | (2006.01) |
| A61K 31/51 | (2006.01) |
| A61K 31/525 | (2006.01) |
| A61K 31/675 | (2006.01) |
| A61K 31/375 | (2006.01) |
| A61K 31/726 | (2006.01) |
| A61K 31/737 | (2006.01) |
| A61K 38/28 | (2006.01) |
| A61K 31/495 | (2006.01) |
| A61K 31/519 | (2006.01) |
| A61K 36/28 | (2006.01) |
| A61K 36/42 | (2006.01) |
| A61K 36/484 | (2006.01) |

(52) U.S. Cl.
CPC .......... *B65D 85/8043* (2013.01); *A61K 31/07* (2013.01); *A61K 31/085* (2013.01); *A61K 31/137* (2013.01); *A61K 31/138* (2013.01); *A61K 31/167* (2013.01); *A61K 31/192* (2013.01); *A61K 31/202* (2013.01); *A61K 31/225* (2013.01); *A61K 31/355* (2013.01); *A61K 31/375* (2013.01); *A61K 31/385* (2013.01); *A61K 31/4045* (2013.01); *A61K 31/4402* (2013.01); *A61K 31/4748* (2013.01); *A61K 31/495* (2013.01); *A61K 31/51* (2013.01); *A61K 31/519* (2013.01); *A61K 31/522* (2013.01); *A61K 31/525* (2013.01); *A61K 31/593* (2013.01); *A61K 31/675* (2013.01); *A61K 31/702* (2013.01); *A61K 31/704* (2013.01); *A61K 31/714* (2013.01); *A61K 31/726* (2013.01); *A61K 31/737* (2013.01); *A61K 36/28* (2013.01); *A61K 36/42* (2013.01); *A61K 36/484* (2013.01); *A61K 38/28* (2013.01)

(58) Field of Classification Search
CPC ............ B65D 85/8043; B65D 85/8046; B65D 85/816; A61K 31/07; A61K 31/085; A61K 31/137; A61K 31/138; A61K 31/167; A61K 31/192; A61K 31/202; A61K 31/225; A61K 31/355; A61K 31/375; A61K 31/385; A61K 31/4045; A61K 31/4402; A47J 31/407; A47J 31/047; A47J 31/06; A47J 31/04; A47J 31/52; A47J 31/56; A47J 31/54; A47J 31/057; A47J 31/02; A47J 31/0573
USPC ......................................... 99/295
See application file for complete search history.

(56) References Cited

U.S. PATENT DOCUMENTS

| 5,811,120 | A | * | 9/1998 | Gibson | .............. A61K 31/4535 424/451 |
|---|---|---|---|---|---|
| 6,478,878 | B1 | * | 11/2002 | Tanaka | .................... B24C 11/00 134/6 |
| 6,758,130 | B2 | * | 7/2004 | Sargent | ...................... A23F 3/14 426/115 |
| 2006/0278093 | A1 | * | 12/2006 | Biderman | ................ A47J 31/40 99/282 |
| 2007/0275146 | A1 | * | 11/2007 | Catani | ....................... A23F 3/34 426/548 |
| 2008/0152768 | A1 | * | 6/2008 | Lan | ....................... B65D 85/816 426/125 |

(Continued)

*Primary Examiner* — Brian W Jennison
(74) *Attorney, Agent, or Firm* — Thomas J. Germinario

(57) ABSTRACT

A system for brewing medicinal beverages, using a cartridge-based beverage formation apparatus, comprises a cartridge containing a beverage composition comprising a mixture of one or more water-soluble active pharmacological treatment agents, such as pain relievers, cold medications, sleeping aids, laxatives, stimulants, or vitamins, and one or more water-soluble non-pharmacological constituents, which can include water-soluble carbohydrates, proteins, alcohols, sweetening, flavoring and coloring agents, anti-caking agents, buffering and acidifying agents, surfactants, thickening and stabilizing agents, antioxidants and/or preservatives.

24 Claims, No Drawings

(56) References Cited

U.S. PATENT DOCUMENTS

| | | | | |
|---|---|---|---|---|
| 2011/0076361 A1* | 3/2011 | Peterson | ............ | B65D 85/8043 |
| | | | | 426/79 |
| 2012/0301581 A1* | 11/2012 | Abegglen | .......... | B65D 85/8043 |
| | | | | 426/112 |
| 2013/0291737 A1* | 11/2013 | Sims | ................. | A47J 31/407 |
| | | | | 99/281 |

* cited by examiner

SYSTEM FOR PREPARING MEDICINAL BEVERAGES USING CARTRIDGE-TYPE BEVERAGE BREWERS

FIELD OF INVENTION

The present invention relates to the field of cartridge-based systems for brewing beverages, and also the field of brewable compositions containing one or more active pharmacological treatment agents.

BACKGROUND OF THE INVENTION

Single-serve coffee brewing systems use individual containers, cartridges, pods, and capsules (hereinafter collectively referred to as "cartridges") to simplify the brewing process by eliminating the need to measure out ingredients from bulk containers. Ingredients are also kept fresher by being sealed within the cartridge rather than stored in a container which is frequently opened.

The present invention applies a cartridge-based brewing system to the preparation of beverages containing active pharmacological treatment agents, such as pain relievers, cold medications, sleeping aids, laxatives, stimulants, and vitamins. Such beverages are hereinafter referred to as "medicinal beverages".

SUMMARY OF THE INVENTION

The present invention is a system for brewing medicinal beverages using a cartridge-based beverage formation apparatus, such as that disclosed in U.S. Pat. No. 9,295,357 B2, the disclosure of which is incorporated herein by reference. The system comprises a cartridge containing a mixture of one or more water-soluble active pharmacological treatment agents, such as pain relievers, cold medications, sleeping aids, laxatives, stimulants, or vitamins, and one or more water-soluble non-pharmacological constituents, which can include water-soluble carbohydrates, proteins, alcohols, sweetening, flavoring and coloring agents, anti-caking agents, buffering and acidifying agents, surfactants, thickening and stabilizing agents, antioxidants and/or preservatives.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

DETAILED DESCRIPTION OF THE PREFERRED EMBODIMENTS

In one embodiment of the present invention, the cartridge contains a beverage composition comprising 0.001 to 6.0 grams of one or more water-soluble active pharmacological treatment agents, mixed with 0.1 to 20 grams of one or more water-soluble non-pharmacological constituents, in powdered or agglomerated form, selected from a group consisting of carbohydrates, alcohols and proteins. The one or more water-soluble non-pharmacological constituents are selected from a group of carbohydrates, alcohols and proteins, consisting of dextrose, fructose, sucrose, sorbitol, mannitol, allulose, polydextrose, soluble dextrins, maltodextrins, corn syrup solids, spray dried or agglomerated natural honey or agave syrup, hydrogenated maltodextrins, maltitol, isomalt, sugar alcohols, milk proteins, hydrolyzed collagen, whey protein isolates, and/or pea proteins.

Preferably, the beverage composition further comprises 0.001 to 1.0 grams of one or more sweetening agents. The one or more sweetening agents are selected from a group consisting of aspartame and its derivatives, sucralose, acesulfame potassium, saccharine, natural *glycyrrhiza* extract, *stevia* extract, and Luo Han Guo fruit extract. Preferably, the beverage composition further comprises 0.01 to 0.5 grams of one or more flavoring agents suitable for use in food and pharmaceutical products. Preferably, the beverage composition further comprises 0.0001 to 0.1 grams of one or more coloring agents suitable for use in food and pharmaceutical products.

Preferably, the beverage composition further comprises 0.01 to 1.0 grams of one or more anti-caking agents, each having a mean particle size of less than 400 microns. The one or more anti-caking agents are selected from a group consisting of silica, calcium silicate, magnesium silicate, and micro-crystalline cellulose.

Preferably, the beverage composition further comprises one or more buffering and acidifying agents. The one or more buffering and acidifying agents are edible organic and inorganic acids and acid salts, selected from a group consisting of citric acid, adipic acid, malic acid, lactic acid, gluconic acid, acetic acid, phosphoric acid, and a respective sodium, calcium and potassium salt of each aforesaid acid.

Preferably, the beverage composition further comprises 0.01 to 0.1 grams of one or more surfactants suitable for use in food and pharmaceutical products. The one or more surfactants are selected from a group consisting of lecithin, milk proteins, natural gums, plant based sterols and their ethylene and propylene oxide condensates, sorbitol esters of fatty acids, glyceryl ester of fatty acids, poly glycerols, ethylene oxide condensates of fatty oils, amino acid amides and ester of fatty acids, and poly ethylene oxide surfactants.

Preferably, the beverage composition further comprises 0.01 to 0.5 grams of one or more thickening and stabilizing agents. The one or more thickening and stabilizing agents are gums selected from a group consisting of xanthan, guar, acacia, alginates, gellan gum, modified cellulose gums, hydrolyzed starch derivatives, carbopoles, poly vinyl pyrrolidones, and malic anhydride copolymers.

In another embodiment of the present invention, the cartridge contains a beverage composition comprising 0.1 to 40.0 grams of an aqueous solution, comprising 0.001 to 6.0 grams of one or more water-soluble active pharmacological treatment agents, mixed with 0.1 to 20 grams of one or more water-soluble non-pharmacological constituents, selected from a group consisting of carbohydrates, amino acids, proteins, and polyhydric alcohols. Preferably, the aqueous solution contains 0.01 to 99.9 percent by weight of water.

Preferably, the carbohydrates are selected from a group consisting of dextrose, fructose, sucrose, sorbitol, mannitol, allulose, polydextrose, soluble dextrins, maltodextrins, corn syrup solids, hydrogenated maltodextrins, maltitol, isomalt, and sugar alcohols.

Preferably, the polyhydric alcohols are selected from a group consisting of glycerin, propylene glycol, water soluble polyethylene glycols, and poly glycerols.

Preferably, the aqueous solution comprises 0.1 to 60 percent by weight of amino acids and proteins. Preferably, the aqueous solution comprises 0.1 to 40 percent by weight of potable ethyl alcohol.

Preferably, the beverage composition further comprises 0.001 to 1.0 gram of one or more sweetening agents selected from a group consisting of aspartame and its derivatives, sucralose, acesulfame potassium, saccharine, natural *glycyrrhiza* extract, *stevia* extract, and Luo Han Guo fruit extract.

Preferably, the beverage composition further comprises one or more thickening and stabilizing agents selected from a group of gums consisting of xanthan, guar, acacia, alginates, gellan gum, modified cellulose gums, hydrolyzed starch derivatives, carbopoles, poly vinyl pyrrolidones, and malic anhydride copolymers.

Preferably, the beverage composition further comprises 0.01 to 2.0 grams of one or more buffering and acidifying agents selected from a group of edible organic and inorganic acids and acid salts consisting of citric acid, adipic acid, malic acid, lactic acid, gluconic acid, acetic acid, phosphoric acid, and a respective sodium, calcium and potassium salt of each aforesaid acid.

Preferably, the beverage composition further comprises one or more surfactants selected from a group consisting of lecithin, milk proteins, natural gums, plant based sterols and their ethylene and propylene oxide condensates, sorbitol esters of fatty acids, glyceryl ester of fatty acids, poly glycerols, ethylene oxide condensates of fatty oils, amino acid amides and ester of fatty acids, and poly ethylene oxide surfactants.

Preferably, the beverage composition further comprises one or more coloring agents, flavoring agents, antioxidants, and preservatives.

Exemplary beverage compositions are formulated as follows:

Pain Relief Hot Beverage for Headache and General Pain

| Acetaminophen USP | 1000 mg |
|---|---|
| Orange flavor | 120 mg |
| FD&C Yellow No 6 dye | 10.0 mg |
| Sucralose | 90.0 mg |
| Citric acid | 600 mg |
| Isomalt | 5000 mg |

Pain Relief Cup for Hot Coffee Beverage Dispenser

| Ibuprofen USP | 400 mg |
|---|---|
| Orange flavor | 120 mg |
| FD&C Yellow No 6 dye | 10.0 mg |
| Sucralose | 90.0 mg |
| Citric acid | 300 mg |
| Isomalt | 5000 mg |

Nighttime Pain Relief Cup for Hot Coffee Beverage Dispenser

| Acetaminophen USP | 650 mg |
|---|---|
| Diphenhydramine HCl USP | 25.0 mg |
| Fruit flavor | 100 mg |
| FD&C Yellow No 6 dye | 10.0 mg |
| Sucralose | 50.0 mg |
| Citric acid | 350 mg |
| Isomalt | 5000 mg |

Daytime Cough and Cold Cup for Hot Coffee Beverage Dispenser

| Acetaminophen USP | 650 mg |
|---|---|
| Dextromethorphan HBr USP | 20.0 mg |
| Phenylephrine HCl USP | 10.0 mg |
| Orange flavor | 120 mg |
| FD&C Yellow No 6 dye | 10.0 mg |
| Sucralose | 70.0 mg |
| Citric acid | 600 mg |
| Allulose | 5000 mg |

Nighttime Cough and Cold Cup for Hot Coffee Beverage Dispenser

| Acetaminophen USP | 650 mg |
|---|---|
| Dextromethorphan HBr USP | 20.0 mg |
| Doxylamine succinate USP | 12.5 mg |
| Honey flavor | 80 mg |
| FD&C Yellow No 6 dye | 10.0 mg |
| Sucralose | 70.0 mg |
| Citric acid | 500 mg |
| Agglomerated sucrose | 5000 mg |

Daytime Pain, Cough, Expectorant, and Decongestant Cup for Hot Beverage Dispenser

| Acetaminophen USP | 500 mg |
|---|---|
| Guaifenesin USP | 200 mg |
| Dextromethorphan HBr USP | 20.0 mg |
| Phenylephrine HCl USP | 10.0 mg |
| Orange flavor | 120 mg |
| FD&C Yellow No 6 dye | 10.0 mg |
| Sucralose | 70.0 mg |
| Citric acid | 600 mg |
| Isomalt | 5000 mg |

Sleeping Medication Cup for Hot Coffee Beverage Dispenser

| Diphenhydramine HCl USP | 50.0 mg |
|---|---|
| Cherry flavor | 70.0 mg |
| FD&C Red No 40 dye | 2.0 mg |
| Sucralose | 70.0 mg |
| Silica | 50.0 mg |
| Citric acid | 600 mg |
| Sorbitol | 6158 mg |

Natural Sleeping Medication Cup for Hot Coffee Beverage Dispenser

| Melatonin USP | 10.0 mg |
|---|---|
| Cherry flavor | 70.0 mg |
| FD&C Red No 40 dye | 2.0 mg |
| Sucralose | 70.0 mg |
| Silica | 50.0 mg |
| Citric acid | 600 mg |
| Sorbitol | 6198 mg |

Laxative Medication Cup for Hot Coffee Beverage Dispenser

| Sennosides A&B | 25.0 mg |
|---|---|
| Vanilla flavor | 70 mg |
| Natural processed Cocoa powder | 1000 mg |
| Sucralose | 70.0 mg |
| Silica | 50.0 mg |
| Agglomerated dextrose | 6785 mg |

Laxative Medication/Stool Softener Cup for Hot Coffee Beverage Dispenser

| | |
|---|---|
| Sennosides A&B | 25.0 mg |
| Docusate sodium | 100.0 mg |
| Vanilla flavor | 70 mg |
| Natural processed Cocoa powder | 1000 mg |
| Sucralose | 70.0 mg |
| Silica | 50.0 mg |
| Agglomerated dextrose | 6785 mg |

Fiber Beverage Cup for Hot Coffee Beverage Dispenser

| | |
|---|---|
| Dextrins | 5000.00 mg |
| Orange flavor | 60 mg |
| FD&C Yellow No 6 dye | 4.0 mg |
| Sucralose | 70.0 mg |
| Citric acid | 400 mg |
| Isomalt | 2000 mg |

Stimulant Beverage Cup for Hot Coffee Beverage Dispenser

| | |
|---|---|
| Caffeine | 100 mg |
| Vanilla flavor | 70.0 mg |
| Natural processed Cocoa powder | 1000 mg |
| Sucralose | 70.0 mg |
| Silica | 50.0 mg |
| Xanthan gum | 250 mg |
| Agglomerated dextrose | 5710 mg |

Multivitamin Beverage Cup for Hot Coffee Beverage Dispenser

| | |
|---|---|
| Vitamin D3 | 0.01 mg |
| Vitamin E | 100 mg |
| Omega 3 fatty acid esters | 160 mg |
| Vitamin A actate | 0.01 mg |
| Alpha lipoic acid | 2.0 mg |
| Vitamin B12 | 0.1 mg |
| Vitamin B1 | 2.0 mg |
| Vitamin B2 | 2.0 mg |
| Vitamin B6 | 2.0 mg |
| Vitamin C | 60.0 mg |
| Vanilla flavor | 70.0 mg |
| Natural processed Cocoa powder | 1000 mg |
| Sucralose | 70.0 mg |
| Silica | 50.0 mg |
| Xanthan gum | 250 mg |
| Agglomerated dextrose | 5000 mg |

Joint Pain Supplement Hot Beverage Pod for Coffee Machine

| | |
|---|---|
| Glucosamine Hydrochloride | 1500.0 mg |
| Chondroitin Sulfate | 200.0 mg |
| Dextrose | 4000.0 mg |
| Sucralose | 60.0 mg |
| Citric acid | 300.0 mg |
| Berry tea flavor | 80.0 mg |
| Silica | 50.0 mg |

Joint Pain Supplement Hot Beverage Pod for Coffee Machine

| | |
|---|---|
| Glucosamine Hydrochloride | 1500.0 mg |
| Chondroitin Sulfate | 200.0 mg |
| Calcium citrate malate | 1000.0 mg |
| Vitamin D3 | 5000 IU |
| Dextrose | 3000.0 mg |
| Sucralose | 60.0 mg |
| Citric acid | 300.0 mg |
| Honey green tea flavor | 100.0 mg |
| Caramel color | 10.0 mg |
| Silica | 50.0 mg |

Soluble Fiber Beverage Cup for Hot Coffee Beverage Dispenser

| | |
|---|---|
| Inulin | 5000.00 mg |
| Vanilla Cream tea flavor | 60 mg |
| Sucralose | 70.0 mg |
| Isomalt | 2000 mg |
| Titanium dioxide | 70.0 mg |
| Disodium phosphate | 100.0 mg |

Anti-Nausea/Motion Sickness/Sea Sickness Beverage Cup for Hot Beverage Dispenser

| | |
|---|---|
| Dimenhydrinate USP | 50.0 mg |
| Cherry flavor | 70.0 mg |
| FD&C Red No 40 dye | 2.0 mg |
| Sucralose | 70.0 mg |
| Silica | 50.0 mg |
| Citric acid | 600 mg |
| Sorbitol | 6200 mg |

Anti-Nausea/Motion Sickness/Sea Sickness Beverage Cup for Hot Coffee Beverage Dispenser

| | |
|---|---|
| Meclizine HCl | 25.0 mg |
| Ginger lemon flavor | 70.0 mg |
| Yellow No 6 dye | 0.5 mg |
| Sucralose | 70.0 mg |
| Silica | 50.0 mg |
| Citric acid | 600.0 mg |
| Sorbitol | 6000 mg |

Natural Anti-Nausea/Motion Sickness/Sea Sickness Beverage Cup for Beverage Dispenser
Ginger Rhizome Extract

| | |
|---|---|
| (Standardized to Gingerol and Shogaols) | 600.0 mg |
| Lemon flavor | 70.0 mg |
| Yellow No 6 dye | 0.5 mg |
| Sucralose | 70.0 mg |
| Silica | 50.0 mg |
| Citric acid | 600.0 mg |
| Sorbitol | 6000 mg |

Menstrual Cramp Treatment Beverage Cup for Hot Coffee Beverage Dispenser

| | |
|---|---|
| Acetaminophen USP | 500.0 mg |
| Pamabrom | 25.0 mg |
| Pyrilamine Maleate | 15.0 mg |
| Cranberry apple flavor | 85.0 mg |
| FD&C Red No 40 dye | 2.0 mg |
| Sucralose | 70.0 mg |
| Silica | 50.0 mg |
| Citric acid | 600 mg |
| Sorbitol | 4200 mg |

Natural Cranberry Extract UTI Treatment Beverage Cup for Hot Coffee Beverage Dispenser

| | |
|---|---|
| Standardized Cranberry extract | 550.0 mg |
| Apple flavor | 50.0 mg |
| Sucralose | 50.0 mg |
| Silica | 50.0 mg |
| Citric acid | 100.0 mg |
| Ascorbic acid | 500.0 mg |
| Sucrose | 8000.0 mg |

Non-Sedating Antihistamine Beverage Cup for Hot Coffee Beverage Dispenser

| | |
|---|---|
| Cetirizine HCl USP | 10.0 mg |
| Cherry flavor | 70.0 mg |
| FD&C Red No 40 dye | 2.0 mg |
| Sucralose | 50.0 mg |
| Silica | 50.0 mg |
| Citric acid | 300.0 mg |
| Sorbitol | 7000.0 mg |

Erectile Dysfunction Treatment Beverage Cup for Hot Coffee Beverage Dispenser

| | |
|---|---|
| Sildenafil Citrate USP | 100.0 mg |
| Vanilla flavor | 70.0 mg |
| Natural processed Cocoa powder | 1000 mg |
| Sucralose | 70.0 mg |
| Silica | 50.0 mg |
| Xanthan gum | 250 mg |
| Agglomerated dextrose | 5710 mg |

Although the preferred embodiments of the present invention have been disclosed for illustrative purposes, those skilled in the art will appreciate that many additions, modifications and substitutions are possible, without departing from the scope and spirit of the present invention as defined by the accompanying claims.

What is claimed is:

1. A system for brewing medicinal beverages using a cartridge-based beverage formation apparatus, the system comprising:
    a cartridge, adapted for use with the cartridge-based beverage formation apparatus;
    contained within the cartridge, a beverage composition consisting essentially of a mixture of one or more water-soluble active pharmacological treatment agents and one or more water-soluble non-pharmacological constituents;
    wherein the beverage composition consists essentially of 0.001 to 6.0 grams of the one or more water-soluble active pharmacological treatment agents, mixed with 0.1 to 20 grams of the one or more water-soluble non-pharmacological constituents, in powdered or agglomerated form; and
    wherein the one or more water-soluble non-pharmacological constituents are selected from the group of carbohydrates, alcohols and proteins, consisting of dextrose, fructose, sucrose, sorbitol, mannitol, allulose, polydextrose, soluble dextrins, maltodextrins, corn syrup solids, spray dried or agglomerated natural honey or agave syrup, hydrogenated maltodextrins, maltitol, isomalt, sugar alcohols, milk proteins, hydrolyzed collagen, whey protein isolates, and pea proteins.

2. The system of claim 1, wherein the one or more water-soluble non-pharmacological constituents further comprise 0.001 to 1.0 grams of one or more sweetening agents.

3. The system of claim 2, wherein the one or more sweetening agents are selected from the group consisting of aspartame and its derivatives, sucralose, acesulfame potassium, saccharine, natural *glycyrrhiza* extract, *stevia* extract, and Luo Han Guo fruit extract.

4. The system of claim 3, wherein the one or more water-soluble non-pharmacological constituents further comprise 0.01 to 0.5 grams of one or more flavoring agents suitable for use in food and pharmaceutical products.

5. The system of claim 4, wherein the one or more water-soluble non-pharmacological constituents further comprise 0.0001 to 0.1 grams of one or more coloring agents suitable for use in food and pharmaceutical products.

6. The system of claim 5, wherein the one or more water-soluble non-pharmacological constituents further comprise 0.01 to 1.0 grams of one or more anti-caking agents, each having a mean particle size of less than 400 microns.

7. The system of claim 6, wherein the one or more anti-caking agents are selected from the group consisting of silica, calcium silicate, magnesium silicate, and micro-crystalline cellulose.

8. The system of claim 7, wherein the one or more water-soluble non-pharmacological constituents further comprise one or more buffering and acidifying agents.

9. The system of claim 8, wherein the one or more buffering and acidifying agents are edible organic and inorganic acids and acid salts, selected from the group consisting of citric acid, adipic acid, malic acid, lactic acid, gluconic acid, acetic acid, phosphoric acid, and the respective sodium, calcium and potassium salts of each aforesaid acid.

10. The system of claim 9, wherein the one or more water-soluble non-pharmacological constituents further comprise 0.01 to 0.1 grams of one or more surfactants suitable for use in food and pharmaceutical products.

11. The system of claim 10, wherein the one or more surfactants are selected from the group consisting of lecithin, milk proteins, natural gums, plant-based sterols and their ethylene and propylene oxide condensates, sorbitol esters of fatty acids, glyceryl ester of fatty acids, poly glycerols, ethylene oxide condensates of fatty oils, amino acid amides and ester of fatty acids, and poly ethylene oxide surfactants.

12. The system of claim 11, wherein the one or more water-soluble non-pharmacological constituents further comprise 0.01 to 0.5 grams of one or more thickening and stabilizing agents.

13. The system of claim 12, wherein the one or more thickening and stabilizing agents are gums selected from the group consisting of xanthan, guar, acacia, alginates, gellan gum, modified cellulose gums, hydrolyzed starch derivatives, carbopoles, poly vinyl pyrrolidones, and malic anhydride copolymers.

14. The system of claim 1, wherein the beverage composition consists essentially of 0.1 to 40.0 grams of an aqueous solution, consisting essentially of 0.001 to 6.0 grams of the one or more water-soluble active pharmacological treatment agents, mixed with 0.1 to 20 grams of the one or more water-soluble non-pharmacological constituents, selected from the group consisting of carbohydrates, amino acids, proteins, and polyhydric alcohols.

15. The system of claim 14, wherein the aqueous solution contains 0.01 to 99.9 percent by weight of water.

16. The system of claim 15, wherein the carbohydrates are selected from the group consisting of dextrose, fructose, sucrose, sorbitol, mannitol, allulose, polydextrose, soluble dextrins, maltodextrins, corn syrup solids, hydrogenated maltodextrins, maltitol, isomalt, and sugar alcohols.

17. The system of claim 16, wherein the polyhydric alcohols are selected the group consisting of glycerin, propylene glycol, water soluble polyethylene glycols, and poly glycerols.

18. The system of claim 17, wherein the aqueous solution comprises 0.1 to 60 percent by weight of amino acids and proteins.

19. The system of claim 18, wherein the aqueous solution comprises 0.1 to 40 percent by weight of potable ethyl alcohol.

20. The system of claim 19, wherein the one or more water-soluble non-pharmacological constituents further comprise 0.001 to 1.0 gram of one or more sweetening agents selected from the group consisting of aspartame and its derivatives, sucralose, acesulfame potassium, saccharine, natural *glycyrrhiza* extract, *stevia* extract, and Luo Han Guo fruit extract.

21. The system of claim 20, wherein the one or more water-soluble non-pharmacological constituents further comprise one or more thickening and stabilizing agents are gums selected from the group consisting of xanthan, guar, acacia, alginates, gellan gum, modified cellulose gums, hydrolyzed starch derivatives, carbopoles, poly vinyl pyrrolidones, and malic anhydride copolymers.

22. The system of claim 21, wherein the one or more water-soluble non-pharmacological constituents further comprise 0.01 to 2.0 grams of one or more buffering and acidifying agents, which are edible organic and inorganic acids and acid salts selected from the group of consisting of citric acid, adipic acid, malic acid, lactic acid, gluconic acid, acetic acid, phosphoric acid, and the respective sodium, calcium and potassium salts of each aforesaid acid.

23. The system of claim 22, wherein the one or more water-soluble non-pharmacological constituents further comprise one or more surfactants selected from the group consisting of lecithin, milk proteins, natural gums, plant based sterols and their ethylene and propylene oxide condensates, sorbitol esters of fatty acids, glyceryl ester of fatty acids, poly glycerols, ethylene oxide condensates of fatty oils, amino acid amides and ester of fatty acids, and poly ethylene oxide surfactants.

24. The system of claim 23, wherein the one or more water-soluble non-pharmacological constituents further comprise one or more coloring agents, flavoring agents, antioxidants, and preservatives.

* * * * *